United States Patent [19]

Svendsen

[11] Patent Number: 4,598,043
[45] Date of Patent: Jul. 1, 1986

[54] METHOD FOR QUANTITATIVELY ASSAYING BLOOD COAGULATION FACTOR XII IN HUMAN PLASMA

[75] Inventor: Lars G. Svendsen, Reinach, Switzerland

[73] Assignee: Pentapharm AG, Basel, Switzerland

[21] Appl. No.: 437,207

[22] Filed: Oct. 28, 1982

[30] Foreign Application Priority Data

Nov. 2, 1981 [CH] Switzerland ............... 6972/81

[51] Int. Cl.$^4$ .............. C12Q 1/56; C07K 5/08
[52] U.S. Cl. ..................... 435/13; 530/381; 435/23; 435/212
[58] Field of Search ............ 435/4, 13, 23, 24, 29, 435/212, 214, 217, 219, 810; 260/112.5; 424/101, 2

[56] References Cited

U.S. PATENT DOCUMENTS

| | | | |
|---|---|---|---|
| 3,884,896 | 5/1975 | Blomback et al. | 435/24 |
| 3,886,136 | 5/1975 | Claeson et al. | 435/24 |
| 4,028,318 | 6/1977 | Aurell et al. | 435/23 |
| 4,137,225 | 1/1979 | Ekenstam et al. | 435/23 |
| 4,169,015 | 9/1979 | Ekenstam et al. | 435/13 |
| 4,214,049 | 7/1980 | Ekenstam et al. | 435/23 |
| 4,275,153 | 6/1981 | Gargiulo et al. | 435/24 |
| 4,278,762 | 7/1981 | Svendsen | 435/13 |
| 4,302,538 | 11/1981 | Autenrieth et al. | 435/13 |
| 4,304,853 | 12/1981 | Jozefonvicz et al. | 435/13 |

OTHER PUBLICATIONS

*Chemical Abstracts*, vol. 98, p. 217, 1983, abstract No. 2358v: Ohishi, S., "Fluid Phase Activation of Hageman Factor (Factor XII) in Citrated Human Plasma by Bromelain: An Application to the Indirect Enzymatic Assay for Hageman Factor".

*Chemical Abstracts*, vol. 97, p. 304, 1982, abstract No. 158494b: Friberger, P. et al, "Chromogenic Substrates for Kallikreins and Related Enzymes".

*Chemical Abstracts*, vol. 74, p. 197, 1971, abstract No. 122220v: Ratnoff, O. D., "Assays for Hageman Factor (Factor XII) and Plasma Thromboplastin Antecedent (Factor XI)".

*Chemical Abstracts*, vol. 91, p. 238, 1979, abstract No. 70529g: Sakuragawa, N. et al, "Studies on the Assay Method for Plasma Prekallikrein".

*Chemical Abstracts*, vol. 95, p. 344, 1981, abstract No. 75935d: Cullmann, W. et al, "Factor XII Assay with the Chromogenic Substrate Chromozym Pk".

*Chemical Abstracts*, vol. 93, p. 311, 1980, abstract No. 182332k: Takamiya, O. et al, "Immunologic Assay for Factor XII by Laurell's Method".

*Chemical Abstracts*, vol. 80, p. 189, 1974, abstract No. 68781n: Webster, M. E. et al, "Interaction of Hageman Factor, Prekallikrein Activator, and Plasmin".

*Methods in Enzymology*, Fujikawa, Lottenberg, vol. 80, "Proteolytic Enzymes", Part C, Lorand, L., ed., Academic Press, New York, pp. 198–211 and 340–361 (1981).

*Chemical Abstracts*, vol. 98, p. 260, 1983, abstract No. 103212y: Alving, B. M., et al, "Plasma Prekallikrein: Quantitative Determination by Direct Activation with Hageman Factor Fragment (B-XIIa)".

*Chemical Abstracts*, vol. 96, p. 319, 1982, abstract No. 157904c: Gallimore, M. J. et al, "Simple Chromogenic Peptide Substrate Assays for Determining Prekallikrein Like Activity in Human Plasma".

*Primary Examiner*—Thomas G. Wiseman
*Assistant Examiner*—M. Moskowitz
*Attorney, Agent, or Firm*—Pennie & Edmonds

[57] ABSTRACT

A method for assaying blood coagulation factor XII in human blood plasma wherein plasma is treated with an activator in order to convert factor XII present in the plasma into factor XIIa, the latter is reacted with a tripeptide derivative which is split by the enzymatic action of factor XIIa and forms a colored or fluorescent split product, and the quantity of this split product is measured photometrically, spectrophotometrically or fluorescence-spectrophotometrically.

6 Claims, No Drawings

METHOD FOR QUANTITATIVELY ASSAYING BLOOD COAGULATION FACTOR XII IN HUMAN PLASMA

BACKGROUND OF THE INVENTION

The present invention relates to a method for quantitatively assaying coagulation factor XII (Hageman factor) in human plasma by activation of factor XII (proenzyme), present in the plasma, to factor XIIa (enzyme), and directly reacting the latter with a substrate capable of being split enzymatically.

Factor XII is the first factor which is activated in the endogenic blood coagulation cascade. Owing to the fact that this factor plays a key role not only in the coagulation system but also in the kallikrein-kinin system and in the fibrinolytic system, it is important to have means for quantitatively assaying this factor in blood plasma. The assaying method most frequently used consists in incubating a plasma sample with kaolin in order to cause maximum activation of the Hageman factor, incubating the activation mixture with plasma deficient in Hageman factor, recalcifying the incubation mixture after a predetermined time by the addition of calcium ions and measuring the coagulation time of the recalcified mixture. The coagulation time is approximately a function of the concentration of Hageman factor in the test sample (see e.g. Oscar D. Ratnoff in "Thrombosis and Bleeding Disorders", 1971, Georg Thieme Verlag, Stuttgart, Germany, pages 215–218). The disadvantage of this assaying method resides in the fact that one measures a value which results from a long cascade of reactions and hence is dependent on a large number of reaction parameters. An additional difficulty results from the fact that plasma deficient in Hageman factor needed for establishing calibration curves is scarcely available.

SUMMARY OF THE INVENTION

It has now been found that the enzymatic activity of factor XIIa formed from factor XII can be assayed directly and quantitatively in blood plasma by using certain chromogenic tripeptide derivatives as substrates capable of being split.

The method of the invention consists in treating plasma with an activator to convert factor XII present in the plasma into factor XIIa, reacting the latter with a tripeptide derivative having the general formula:

$$H-D-N-\underset{R^2}{\underset{|}{CH}}-\underset{R^3}{\underset{|}{\overset{O}{\overset{\|}{C}}}}-N-\underset{R^4}{\underset{|}{CH}}-\underset{R^5}{\underset{|}{\overset{O}{\overset{\|}{C}}}}-Arg-R^1$$

wherein
  $R^1$ represents a chromogenic or fluorogenic substituted amino group capable of being split off enzymatically,
  $R^2$ represents hydrogen, $R^3$ represents a straight chain or branched alkyl radical having 1 to 4 carbon atoms or a benzyl, p-hydroxybenzyl, cyclohexylmethyl or 4-hydroxycyclohexylmethyl radical, and $R^4$ and $R^5$ represent hydrogen, or
  $R^2$ represents hydrogen and $R^4$ and $R^5$, together, represent an alkylene radical having 3 or 4 carbon atoms and $R^3$ has the meaning stated above, or
  $R^2$ and $R^3$, together, represent an alkylene radical having 3 or 4 carbon atoms, $R^4$ represents hydrogen and $R^5$ has the same meaning as $R^3$, or with a salt thereof with an acid, and measuring the quantity of colored or fluorescent split product $R^1H$ released enzymatically from the tripeptide derivative by factor XIIa by photometric, spectrophotometric or fluorescencespectrophotometric methods.

DETAILED DESCRIPTION OF THE INVENTION

Kaolin or a preparation containing cephalin and ellagic acid can, for example, be used as the activator. The activation of factor XII is conveniently carried out at about 0° C. The reaction of factor XIIa with the tripeptide derivative is preferably carried out in the presence of soybean trypsin inhibitor in a buffer system at a pH of 7.4 to 8.0, preferably 7.7, and at an ionic strength of 0.025 to 0.2, preferably 0.05.

The salts of the tripeptide derivatives can be salts with mineral acids, e.g. HCL, HBr, $H_2SO_4$ or $H_3PO_4$, or with an organic acid, e.g. formic, acetic, propionic, lactic, citric, oxalic, tartaric, benzoic, phthalic, tricholoroacetic or trifluoroacetic acid.

The tripeptide derivatives used according to the invention can be prepared by methods known per se.

The following individual tripeptide derivatives are comprised by the above general formula: 2AcOH.H-D-Ala-Gly-Arg-pNA, 2AcOH.H-D-But-Gly-Arg-pNA, 2AcOH.H-D-Val-Gly-Arg-pNA, 2AcOH.H-D-Nval-Gly-Arg-pNA, 2AcOH.H-D-Leu-Gly-Arg-pNA, 2AcOH.H-D-Nleu-Gly-Arg-pNA, 2AcOH.H-D-Ile-Gly-Arg-pNA, 2AcOH.H-D-Phe-Gly-Arg-pNA, 2AcOH.H-D-Tyr-Gly-Arg-pNA, 2AcOH.H-D-CHA-Gly-Arg-pNA, 2AcOH.H-D-CHT-Gly-Arg-pNA, 2AcOH.H-D-Phe-Pro-Arg-pNA, 2AcOH.H-D-Tyr-Pro-Arg-pNA, 2AcOH.H-D-CHA-Pro-Arg-pNA, 2AcOH.H-D-CHT-Pro-Arg-pNA, 2AcOH.H-D-CHA-Pip-Arg-pNA, 2AcOH.H-D-CHT-Pip-Arg-pNA, 2AcOH.H-D-Pro-Phe-Arg-pNA, 2AcOH.H-D-Pro-Tyr-Arg-pNA, 2AcOH.H-D-Pro-CHA-Arg-pNA, 2AcOH.H-D-Pro-CHT-Arg-pNA, 2AcOH.H-D-Pip-Phe-Arg-pNA, 2AcOH.H-D-Pip-Tyr-Arg-pNA, 2AcOH.H-D-Pip-CHA-Arg-pNA and 2AcOH.H-D-Pip-CHT-Arg-pNA.

The abbreviations used in the above list have the following meaning:
  AcOH=acetic acid
  Ala=alanyl
  Arg=arginyl
  But=α-aminobutyryl
  CHA=3-cyclohexyl-alanyl
  CHT=3-(4-hydroxycyclohexyl)-alanyl
  Gly=glycyl
  Ile=isoleucyl
  Leu=leucyl
  Nleu=norleucycl
  Nval=norvalyl
  Phe=phenylalanyl
  Pip=pipecolinoyl
  Pro =prolyl
  Tyr=tyrosyl
  Val= valyl The two amino acid groups attached to the D-amino acid group have the L-form.

The above mentioned tripeptide derivatives are compounds known per se in which the p-nitrophenylamino group can be replaced by another chromogenic or fluorogenic substituted amino group, e.g. by a 1-carboxy-2-nitro-phen-5-ylamino, 1-sulfo-2-nitro-phen-5-ylamino, β-naphthylamino, 4-methoxy-β-naphthylamino, 5-nitro-α-naphthylamino, quinon-5-ylamino, 8-nitro-quinon-5-ylamino, 4-methyl-coumar-7-ylamino or 1,3-di(methoxycarbonyl)-phen-5-ylamino group (derived from dimethyl 5-amino-isophthalate).

The process of the invention can be carried out as follows:

For assaying factor XII in citrate plasma the latter is mixed with an aqueous preparation containing cephalin and ellagic acid, e.g. Actin ® (manufactured by DADE, Miami, USA) or Cephotest ® (manufactured by Nyegaard & Co. AS., Oslo, Norway), and the mixture is incubated for a few minutes, preferably 4 minutes, at low temperature, preferably 0° C., in order to convert factor XII into factor XIIa. The use of low temperatures is important in order to avoid the formation of enzyme complexes with the plasma inhibitor $a_2$-macroglobulin since these complexes might enzymatically split the tripeptide derivatives used as substrates, although at lower rates than the corresponding free enzymes. Then an aliquot part of the obtained activation mixture is added to a test system prepared by mixing a buffer, e.g. tris-imidazole buffer having a pH of 7.4 to 8.0, preferably 7.7, and an ionic strength of 0.025 to 0.2, preferably 0.05, and containing soybean trypsin inhibitor, with an aqueous solution of one of the above defined tripeptide derivatives and an aqueous solution of the activator (Actin ® or Cephotest ®) and pre-incubating the mixture for a few minutes at the temperature at which the splitting of the tripeptide derivative is to be measured. Then the quantity of colored or fluorescent split product released per time unit is measured by photometric, spectrophotometric or fluorescence-spectrophotometric methods. If the split product is p-nitroaniline, the measurement is preferably carried out at 405 nm.

The soybean trypsin inhibitor present in the test system has the function of selectively inhibiting the plasma kallikrein activated concurrently with the activation of factor XII to factor XIIa so as to prevent its enzymatic action on the tripeptide derivative used as substrate. On the other hand, soybean trypsin inhibitor has no inhibiting action on factor XIIa.

The assaying method of the invention has several advantages as compared to the known older assaying method inasmuch as it provides a direct assaying of factor XII via activated factor XIIa whose enzymatic activity can be determined in one single step by means of the above defined tripeptide derivatives. In the older method the activity of factor XIIa was measured indirectly by means of the coagulation time. The coagulation does not occur before the complete endogenic coagulation cascade triggered by factor XIIa is terminated. In order to obtain comparable assaying values it is necessary to use plasma deficient in Hageman factor for determining the influence of factor XIIa on the coagulation time and establishing calibration curves therefor. The older method in which the final result of measurement is obtained only after completion of complicated interacting enzymatic processes comprises numerous uncontrollable sources of errors and hence is not accurate. It is extremely difficult to obtain a plasma which is completely deficient in factor XII. In these days clinical laboratories tend to use automatic analytical instruments by which analyses can be carried out quickly and accurately with a minimum of staff. The assaying method of the invention is particularly well adapted for use in such automatic analytical instruments, whereas the older method can only be carried out manually and semi-quantitatively by trained laboratory staff in a time-consuming manner.

The process of the invention can be carried out in the manner described in the following Example.

EXAMPLE

A test system consisting of 0.75 ml of tris-imidazole buffer having a pH of 7.7 and an ionic strength of 0.05 and containing 0.1 mg of soybean trypsin inhibitor per ml, 0.25 ml of $2 \times 10^{-3}$ molar aqueous solution of 2A-cOH.H-D-Leu-Gly-Arg-pNA and 0.20 ml of aqueous activated cephaloplastin reagent (Actin ® manufactured by DADE, Miami, USA) is pre-incubated for 4 minutes at 37° C. To the pre-incubate is added 0.05 ml of an incubate obtained by mixing 0.1 ml of normal citrate plasma and 0.2 ml of aqueous activated cephaloplastin reagent and incubation for 4 minutes at 0° C. After mixing the two components the quantity of p-nitroaniline released by factor XIIa is continuously measured spectrophotometrically at 405 nm during 5 minutes. The activity of factor XIIa is calculated in enzyme units per ml of plasma from the increase in the optical density per minute.

By this method an average of 0.15 to 0.30 enzyme units of factor XIIa per ml is measured in normal plasma. Since one molecule of factor XII yields one molecule of factor XIIa as a result of the activation the values determined for factor XIIa are at the same time a measure of the quantity of factor XII initially present in the plasma.

I claim:

1. A method for quantitatively assaying blood coagulation factor XII directly from human blood plasma which comprises
   (a) contacting unpurified human blood plasma with an activator in order to quantitatively convert any factor XII present in the plasma to factor XIIa;
   (b) reacting the unpurified plasma which contains unpurified factor XIIa with a tripeptide derivative having the general formula H-D-X-Gly-Arg-R¹ wherein the $R^1$ radical is a chromogenic or fluorogenic substituted amino group which is cleavable by the enzymatic action of factor XIIa, and X represents an amino acid selected from the group consisting of α-aminobutyric acid, norvaline, leucine, norleucine, phenylalanine, tyrosine, hexahydrophenylalanine and hexahydrotyrosine, or with a mineral or organic acid salt of the tripeptide derivative; and
   (c) measuring the quanitity of colored or fluorescent split product $R^1H$ released enzymatically from the tripeptide derivative or salt thereof by factor XIIa by photometric, spectrophotometric or fluorescence-spectrophotometric methods, so as to quantitatively assay blood coagulation factor XII directly from human blood plasma.

2. The method according to claim 1 wherein the activator is selected from the group consisting of kaolin and a preparation of cephalin and ellagic acid.

3. The method according to claim 2 wherein the reaction of factor XIIa with the tripeptide derivative is carried out in the presence of soybean trypsin inhibitor.

4. The method according to claim 3 wherein the reaction is carried out in a buffer system at a pH of 7.4 to 8.0 and an ionic strength of 0.025 to 0.2.

5. The method according to claim 4 wherein the activation of factor XII is carried out at 0° C.

6. The method according to claim 5 wherein the R' radical is selected from the group consisting of a p-nitrophenylamino, 1-carboxy-2-nitro-phen-5-ylamino, 1-sulfo-2-nitrophen-5-ylamino, β-napthylamino, 4-methoxy-β-naphthylamino, 5nitro-naphthylamino, quinon-5-ylamino, 8-nitro-quinon-5-ylamino, 4-methyl-coumar-7-ylamino and 1,3-di(methoxy-carbonyl)-phen-5-ylamino (derived from dimethyl 5-amino-isophthalate).

* * * * *